(12) United States Patent
Sirigu et al.

(10) Patent No.: US 10,779,726 B2
(45) Date of Patent: Sep. 22, 2020

(54) DEVICE AND METHOD FOR DETERMINING EYE MOVEMENTS BY TACTILE INTERFACE

(71) Applicants: CENTRE NATIONAL DE LA RECHERCHE SCIENTIFIQUE, Paris (FR); UNIVERSITÉ CLAUDE BERNARD LYON 1, Villeurbanne (FR)

(72) Inventors: Angela Sirigu, Paris (FR); Jean-René Duhamel, Paris (FR); Guillaume Lio, Paris (FR)

(73) Assignees: Centre National de la Recherche Scientifique, Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 233 days.

(21) Appl. No.: 16/069,297

(22) PCT Filed: Dec. 27, 2016

(86) PCT No.: PCT/EP2016/082730
§ 371 (c)(1),
(2) Date: Jul. 11, 2018

(87) PCT Pub. No.: WO2017/121617
PCT Pub. Date: Jul. 20, 2017

(65) Prior Publication Data
US 2019/0021589 A1 Jan. 24, 2019

(30) Foreign Application Priority Data

Jan. 15, 2016 (EP) .................................... 16305042

(51) Int. Cl.
*A61B 3/113* (2006.01)
*A61B 3/024* (2006.01)
(Continued)

(52) U.S. Cl.
CPC ............ *A61B 3/113* (2013.01); *A61B 3/0033* (2013.01); *A61B 3/0041* (2013.01); *A61B 3/024* (2013.01);
(Continued)

(58) Field of Classification Search
CPC ..... A61B 3/113; A61B 3/0033; A61B 3/0041; A61B 3/024; A61B 5/163; G06F 3/013;
(Continued)

(56) References Cited

U.S. PATENT DOCUMENTS

| 5,668,622 A | 9/1997 | Charbonnier et al. |
| 2011/0205167 A1 | 8/2011 | Massengill |

(Continued)

FOREIGN PATENT DOCUMENTS

CN 101657846 A 2/2010

*Primary Examiner* — Daniel L Cerioni
*Assistant Examiner* — Raymond P Dulman
(74) *Attorney, Agent, or Firm* — Occhiuti & Rohlicek LLP

(57) ABSTRACT

An eye-movement determination method includes providing an a touch display and a memory that stores an image that includes a point of interest, wherein the image is a stored image, and repeatedly executing a set of steps. The steps include determining a position of a contact point, locating a corresponding position in an image that is displayed on the touch display, generating a degraded image from the stored image, displaying the degraded image on the touch display, and recording successive positions of the contact point. The contact point is a point at which a user contacts the touch display. The degraded image is substantially identical to the stored image with a clear zone but degrades beyond the clear zone.

10 Claims, 5 Drawing Sheets

(51) Int. Cl.
  *G06F 3/01* (2006.01)
  *G06F 3/0488* (2013.01)
  *G06F 3/038* (2013.01)
  *A61B 5/16* (2006.01)
  *A61B 3/00* (2006.01)

(52) U.S. Cl.
  CPC .............. *A61B 5/163* (2017.08); *G06F 3/013* (2013.01); *G06F 3/038* (2013.01); *G06F 3/0488* (2013.01); *G06F 2203/0381* (2013.01)

(58) Field of Classification Search
  CPC ...... G06F 3/048; G06F 3/0487; G06F 3/0488; G06F 2203/0381
  See application file for complete search history.

(56) References Cited

U.S. PATENT DOCUMENTS

| | | | |
|---|---|---|---|
| 2011/0270123 A1 | 11/2011 | Reiner | |
| 2014/0198297 A1* | 7/2014 | Bathiche | A61B 3/08 351/203 |
| 2016/0179236 A1* | 6/2016 | Shin | G06F 1/1616 345/173 |
| 2017/0360295 A1* | 12/2017 | Oz | G06K 9/3233 |

* cited by examiner

Fig. 3
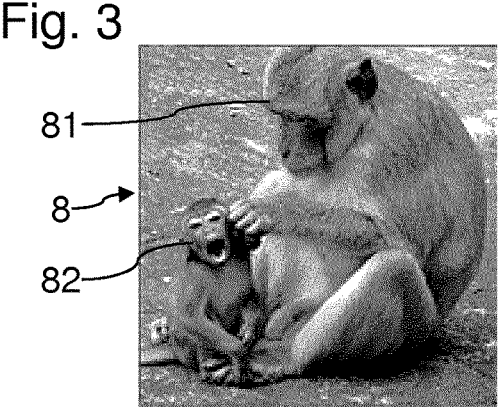
Fig. 4
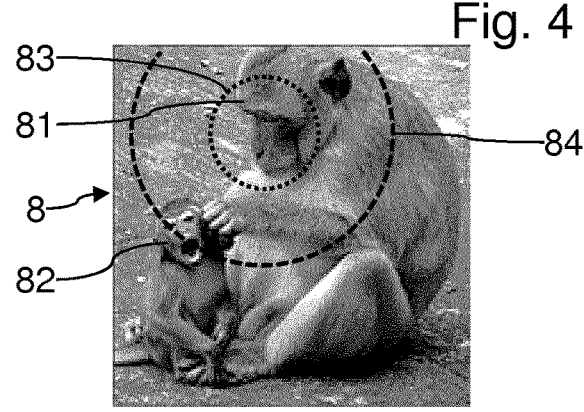
Fig. 5
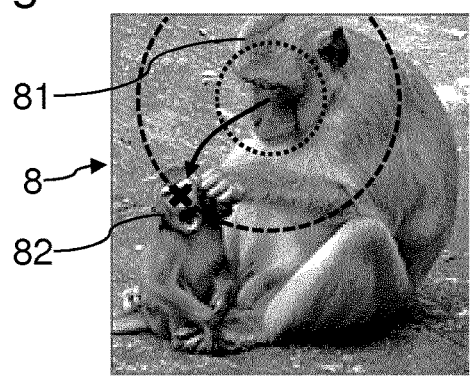
Fig. 6
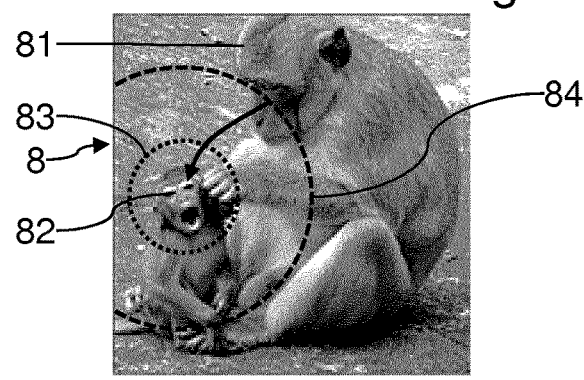
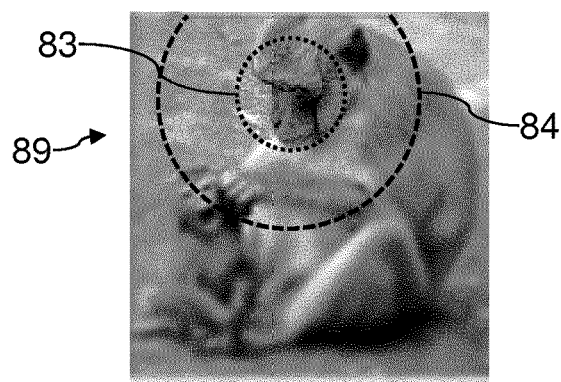
Fig. 7

DEVICE AND METHOD FOR DETERMINING EYE MOVEMENTS BY TACTILE INTERFACE

RELATED APPLICATIONS

This application is the national stage entry under 35 USC 371 of international application PCT/EP2016/082730, filed on Dec. 27, 2016, which claims the benefit of the Jan. 15, 2016 priority date of European application EP16305042.0, the contents of which are incorporated by reference.

FIELD OF INVENTION

The invention relates to oculometry, and in particular, to recording eye movements.

BACKGROUND

The human eye explores visual space by carrying out a visual or ocular exploration sequence. This is often called "visual exploration."

Each such sequence includes rapid movements of the gaze, called ocular saccades, that alternate with relatively long periods of fixation of the gaze. These movements are necessary because, at any instant, the retinal image is clear only in a range of a few degrees of visual angle corresponding to the central region of the retina, which is called the fovea. The subjective sensation of having a large, colored, and detailed visual field with an angle of about 120° in fact results from a construction process in which the cortex integrates successive views obtained through visual or ocular exploration sequences.

Visual exploration is a natural and unconscious task that is continuously carried out by the human eye. Optimized visual exploration requires a great many perceptive, motor, and cognitive capacities. Thus, recording, quantifying and analyzing ocular behavior is useful for detecting those pathologies that result in characteristic visual explorations.

By way of example, a behavior characterized by avoidance of eye contact may be characteristic of disorders on the autistic spectrum and a visual exploration focused on half of a scene will possibly indicate unilateral spatial neglect.

Thus, from a clinical point of view, oculometry is a method that has great potential for diagnosing and monitoring neuro-psychiatric pathologies.

Visual exploration is also a good way to predict actions. For example, a good defensive basketball player will observe a dribbling opponent's eyes to guess where he will pass the ball next. A goalkeeper will observe a kicker's eyes to plan where he will leap to block the kick. An object is often observed before being picked up and, likewise, an object that has not been seen is not picked up. These examples makes oculometry a tool that is widely used, in ergonomics, to optimize human-machine interfaces, product packaging, or publicity documents.

A device used to observe a subject's visual exploration is often called an "oculometer." Conventional oculometers are complex devices that often include high-speed cameras, infrared illuminators, computational processors and a suitable software suite. Such oculometry devices take precise measurements of the ocular exploration but have a very high acquisition cost and cost of use. Such oculometry devices are therefore not accessible to the general public. Because of the limitation of the access to such devices, it is difficult to carry out studies with a sufficient number of observers to guarantee their reliability.

Moreover, such oculometers must be used in a controlled environment with calibration phases that place constraints on the subject's movement. These requirements are often incompatible with certain pathologies or with subjects having short concentration spans, such as children. In many cases, the subject is positioned at a controlled distance from the display and must remain still with his chin resting on an orthoptic chin-rest for an extended period.

SUMMARY

The invention aims to solve one or more of these drawbacks. The invention thus relates to a device and method for determining eye movements.

In one aspect, the invention features a non-abstract method comprising determining eye movements, wherein determining eye movements comprises providing an apparatus, executing a set of steps and repeating execution of the set of steps, wherein the apparatus comprises a touch display and a memory that stores an image that includes a point-of-interest, wherein the image is a stored image, wherein the set of steps comprises determining a position of a contact point, locating a corresponding position in an image that is displayed on the touch display, generating a degraded image from the stored image, displaying the degraded image on the touch display, and recording successive positions of the contact point, wherein the contact point is a point at which a subject contacts the touch display, wherein the degraded image is substantially identical to the stored image with a clear zone, wherein the clear zone includes the contact point and surroundings thereof, and wherein the image is degraded beyond the clear zone using a peripheral degradation parameter.

Like all methods, methods of determining eye movements can presumably be carried out abstractly and non-abstractly. The description only purports to describe a non-abstract implementation. A description of an abstract implementation has been omitted. Thus, the claims, when properly construed in light of the specification, only cover non-abstract implementations of the method. To the extent the claims are seen to cover abstract implementations, those implementations are hereby disclaimed. Applicant, acting as his own lexicographer, hereby defines the claims so that they cover only non-abstract implementations of the method and only non-abstract implementations of devices for carrying out the method. As such the claims specifically exclude any and all abstract implementations of the methods recited therein.

The claims as recited herein represent an improvement in technology. Specifically, the claims recite an improvement in medical technology and more specifically, in the technology of oculometry.

BRIEF DESCRIPTION OF THE DRAWINGS

Other features and advantages of the invention will become more apparent from the description that is given thereof below, by way of completely non-limiting indication, and with reference to the appended drawings, in which:

FIGS. 3 to 6 illustrate an image and an example of an eye movement dependent on centers of interest of the image;

FIG. 7 illustrates an example of the instantaneous perception of the image of FIG. 3 when a center of interest is being focused on;

DETAILED DESCRIPTION

Figure 1:
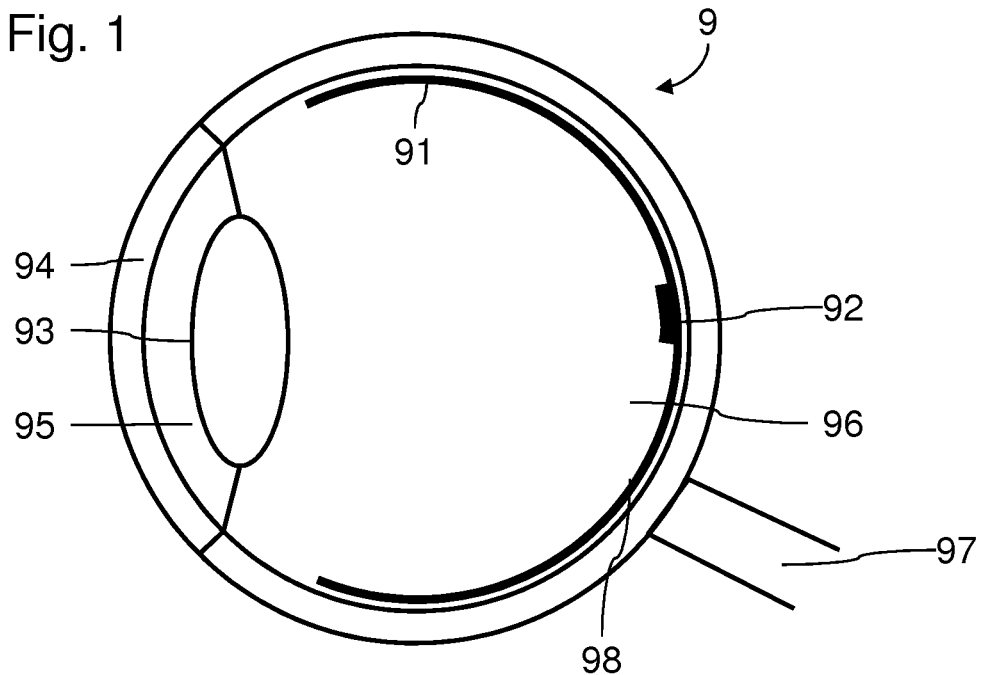
FIG. 1 is a schematic cross-sectional view of a human eye.

FIG. 1 is a schematic cross-sectional view of a human eye 9. Light enters the eye via the cornea 94, passes through the aqueous humor 95, the crystalline lens 93, and then through the vitreous humor 96 before reaching the photoreceptors on the retina 91 A blind spot 98 is defined at the optic nerve 97.

Binocular human vision extends over an angle of about 120°. But it is only within a small portion of this field that humans fully perceive details and colors. This portion corresponds to light that illuminates the foveal region 92 of the retina 91. The foveal region intercepts light that is incident with a cone half-angle of between 1° and 2°. As one proceeds along the retina 91 away from the foveal region 91, the density of photoreceptors greatly decreases, firstly in a parafoveal region that extends as far as a cone half-angle of about 5°, then in a peripheral region which extends to a cone half-angle larger than 5°.

Figure 2:
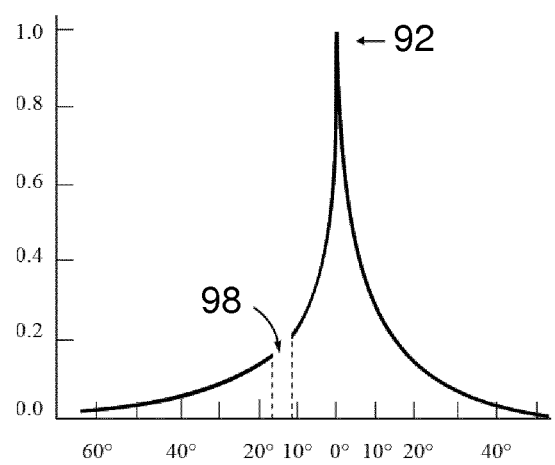
FIG. 2 is a graph of relative visual acuity as a function of an angle with respect to the fovea.

FIG. 2 shows relative visual acuity along the vertical axis and angle relative to the foveal region on the horizontal axis. As is apparent from the figure, the acuity of human vision diminishes rapidly as one leaves the foveal region 92.

Despite this, a human perceives the environment is colored and very detailed. To achieve this, the oculomotor system causes the eyes to continuously explore the scene and thus to capture multiple images. The brain then assembles the resulting images and integrates them. The overall image of which a human is conscious is thus the result of the brain having integrated the results of continuous visual exploration of the environment by the oculomotor system. A great deal of information regarding a possible cognitive impairment is thus obtained by recording eye movements.

In particular, despite the rapid decrease in the density of photoreceptors in the retina, the human oculomotor system is capable of extracting a great deal of information from the peripheral region in order to guide oculomotor exploration behavior.

FIG. 3 illustrates an image 8 comprising a plurality of points-of-interest. The main points-of-interest in this image 8 are an adult-monkey's face 81 and a juvenile-monkey's face 82. FIGS. 4 to 6 illustrate an example of ocular movement dependent on these points-of-interest.

In FIG. 4, the image 8 is presented to a subject. The subject's attention and gaze fall upon the adult-monkey's face 81. Within a foveal region 83, which includes the adult-monkey's face 81 and which corresponds to the retina's foveal region 92, the subject enjoys clear vision. Within a parafoveal region 84 that encircles the foveal region 83, the subject's visual resolution is clearly lower. Beyond the parafoveal region 84 is a peripheral region in which the subject's visual resolution is even lower.

FIG. 7 illustrates the subject's perception 89 of the image 8 of FIG. 3 when the foveal region 83 is centered on the adult-monkey's face 81. The subject perceives the foveal region 83 as clear, the parafoveal region 84 as slightly blurred, and the peripheral region as even more blurred.

In FIG. 5, on the basis of the high-resolution information of the foveal region 83 and of the low-resolution information of the peripheral vision, the subject is able to recognize the juvenile monkey's face 82 as another point-of-interest in the image 8.

As illustrated in FIG. 6, in order to obtain a detailed vision of this other point-of-interest, a rapid eye movement, called a saccade, moves the foveal region 83 to the juvenile monkey's face 82.

Figure 8:
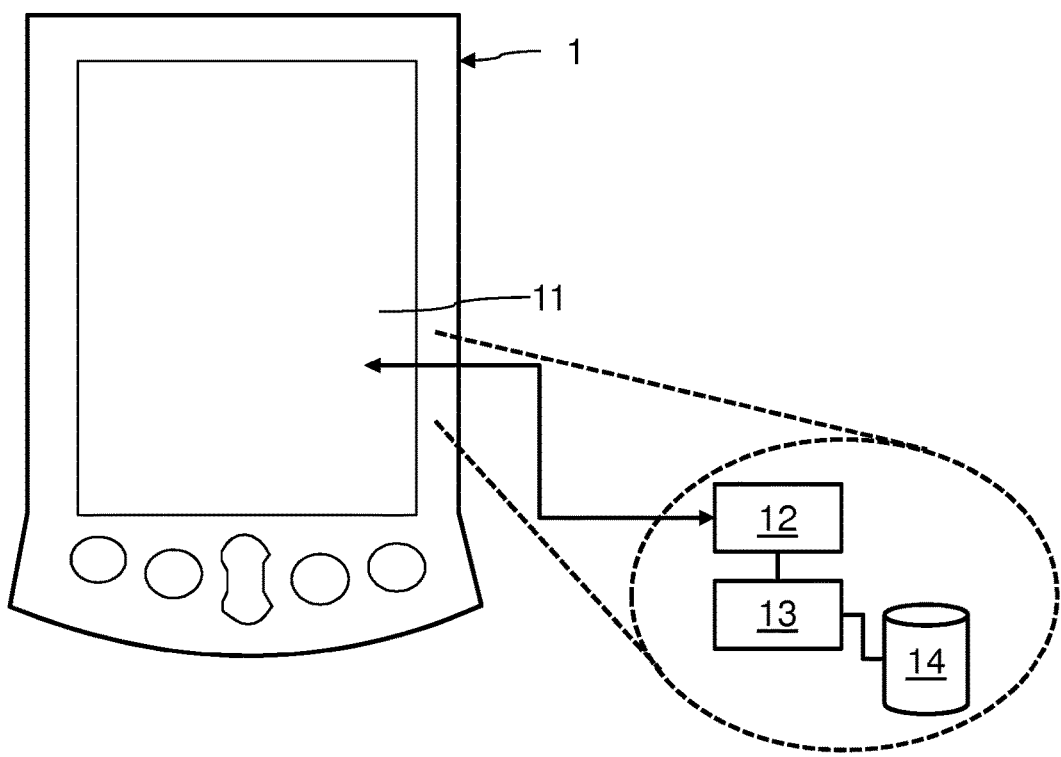
FIG. 8 is a schematic representation of a device for determining eye movements according to one example embodiment of the invention.

FIG. 8 shows an example of an apparatus 1 for determining eye movements by displaying, on a touch display 11, a degraded image, corresponding to FIG. 7 on the basis of a stored image corresponding to FIG. 3. The degraded image aims to reproduce the degradation in visual acuity that is observed when passing from the foveal region 83 to the peripheral region.

In the embodiment shown in FIG. 8, the apparatus 1 is implemented in the form of a cell phone or a touch tablet having a touch display 11 and a digital memory 14 that stores one or more images. Each stored image includes one or more points-of-interest. The images may be delivered by a remote server and be stored only temporarily in the digital memory 14.

The apparatus 1 moreover also includes a processing device 13, for example implemented in the form of a processor controlled by a software application. The processing device 13 reads images stored in the digital memory 14.

The apparatus 1 moreover comprises a communication interface 12, for controlling the touch display 11 and for collecting the coordinates of a point-of-contact, or "contact point," on the touch display 11. The communication interface 12 connects to the processing device 13. An apparatus 1 that relies on commonly-available hardware may therefore be used, thereby allowing implementation at a low cost.

Figure 9:
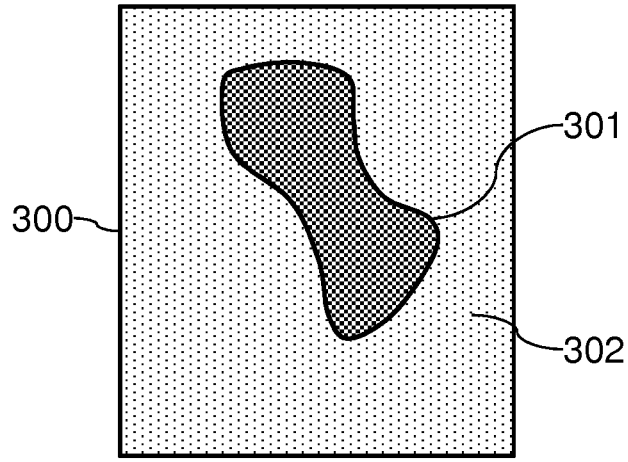
FIG. 9 is a representation of an example of an image stored in a device for determining eye movements.

FIG. 9 illustrates a simplified example of a stored image 300 that has been stored in the memory 14. The stored image 300 includes a point-of-interest 301. The point-of-interest 301 has, for example, a small area and a color or light contrast with respect to a background 302 of the stored image 300. In the illustrated example, the point-of-interest 301 is an area that lies inside a curved line that is darker and smaller than a dotted background 302. The stored image 300 is provided solely by way of illustration. Any other image including one or more points-of-interest is also usable.

Figure 10:
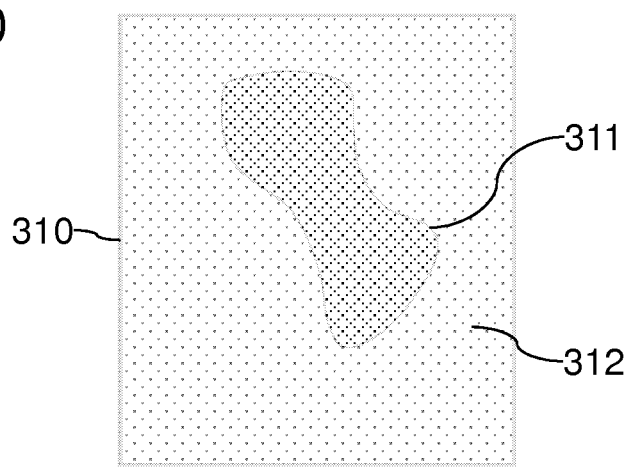
FIG. 10 is a representation of a completely blurred image generated from the stored image in FIG. 9.

FIG. 10 illustrates an integrally-degraded image 310 generated from the stored image 300. In an integrally degraded image, 100% of the area of the image has been degraded. The integrally-degraded image 310 shown herein is generated by blurring the entirety of the area of the stored image 300. The integrally-degraded image 310 thus includes a first blurred-zone 311 corresponding to the blurring the image's point-of-interest 301 and a second blurred-zone 312 corresponding to blurring the image's background 302.

The integrally-degraded image 310 may be the first image displayed on the touch display 11 with a view to determining visual exploration by measurements of touch exploration. This integrally-degraded image 310 may thus serve to initiate the touch exploration with the subject possibly distinguishing the first blurred-zone 311 corresponding to the point-of-interest 301. The first point-of-contact of the subject will therefore very probably be positioned in the first blurred-zone 311.

Figure 11:
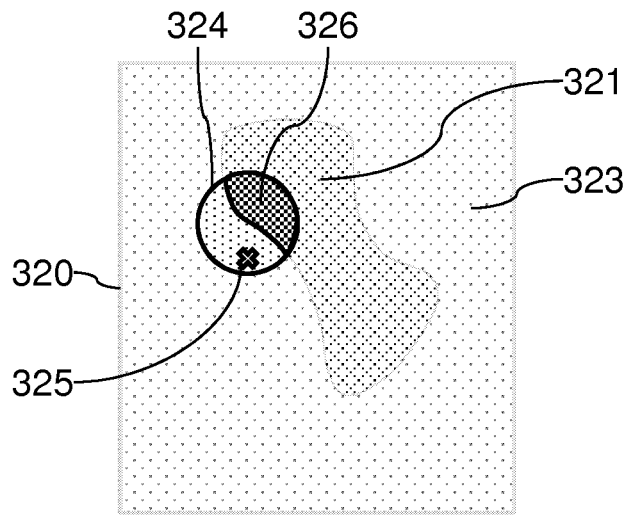
FIG. 11 is a representation of an example of an image displayed depending on the point-of-contact of the subject with the device for determining eye movements.

FIG. 11 illustrates a partially-degraded image 320 that has been generated from the stored image 300.

Figure 12:
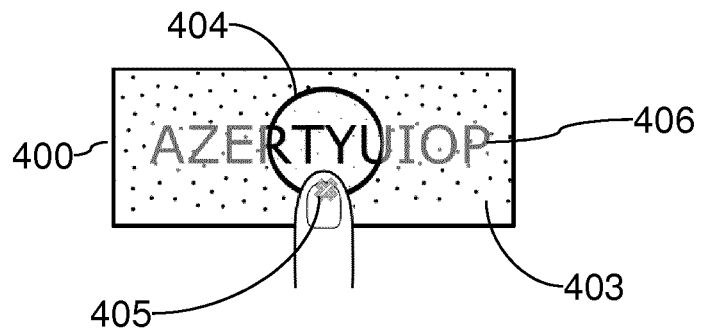
FIG. 12 is an example of a degraded image generated from an image containing alphanumeric information.

The partially-degraded image 320 includes a clear zone 324 in which the image 320 is substantially identical to the stored image 300. A portion 326 of the point-of-interest extends into the clear zone 324. The apparatus 1 determines the position of the last point-of-contact 325 with respect to the image currently being displayed and positions the clear zone 324 to include the position of the last point-of-contact 325 and its surroundings. For ergonomic reasons, the apparatus 1 positions the clear zone 324 above the point-of-contact 325, as shown in FIG. 12. This avoids having the subject's finger mask clear zone 324. Although the figure shows the subject's finger defining the point-of-contact 325 defined by the subject's finger, it is possible to define the point-of-contact using a stylus or any other pointing device.

Referring back to FIG. 11, the partially-degraded image 320 includes a degraded zone 323 peripheral to the clear zone 324. The degraded zone 321 corresponds to the first blurred-zone 311 of the point-of-interest 301 present in the degraded zone 323.

The degradation of the clear zone 324 allows display of information about other zones of the point-of-interest 301 and also information corresponding to peripheral vision. This tends to promote exploratory behavior, which tends to arise from a natural desire to discover what information the display contains.

The degradation of the clear zone 324 also motivates the subject to perform a touch exploration of the degraded zone 323 with a view to discovering this information. The touch movement corresponds to an ocular exploration. If the peripheral image were clear, the subject could perform a visual exploration of the displayed image without moving his finger.

The apparatus 1 degrades the image so that, within the degraded zone 323, it renders the image's microstructures imperceptible while preserving its macrostructures. In particular, the apparatus 1 preserves enough of the macrostructures to be detectable in peripheral vision and to thereby provoke the subject's visual exploration of the image.

In practice, the apparatus 1 begins a method for determining eye movements by displaying the integrally-degraded image 310 on the touch display 11. Then, after having determined a point-of-contact 325 with the touch display 11, it locates the corresponding position with respect to the integrally-degraded image 310. This determination of the first contact optionally triggers a countdown in order to limit the duration of the method. The method continues with launching the determination of the eye movements with the display of the integrally-degraded image 310 on the touch display 11.

Once a point-of-contact 325 with the touch display 11 has been determined, the method continues with locating the corresponding position with respect to the integrally-degraded image 310. This determination of the first contact optionally triggers a countdown in order to limit the duration of the method.

The method continues with generating a first degraded image 320 from the stored image 300. Within this image, the clear zone 324 includes the determined position of the point-of-contact 325 and its surroundings and the degraded zone 323 corresponding to the degradation of the stored image 300 with a peripheral degradation parameter.

The method then continues with repeating certain successive steps. These steps include determining the position of the last point-of-contact 325 with the touch display 11 and locating the corresponding position in the degraded image currently being displayed; recording the position of the last point-of-contact 325 with the touch display 11; generating a new degraded image 320 from the stored image 300, the new degraded image being substantially identical to the stored image 300 in the clear zone 324 that includes the position of the last point-of-contact 325 and its surroundings, the degraded zone 323 corresponding to the degradation of the stored image 300 with the peripheral degradation parameter; displaying, on the touch display 11, the new degraded image 320; and verifying whether a condition for ending the test has been met (for example whether the touch exploration duration has reached a preset threshold or whether the touch exploration distance has reached a preset threshold).

The degradation between a stored image 300 and a degraded image 320 may be determined by means of an SSIM index, using the method described in the publication entitled "Image Quality Assessment: From Error Visibility to Structural Similarity," published by Mrs. Zhou Wang et al. 4 Apr. 2004 in IEEE Transactions on Image Processing, volume 13 number 4.

The clear zone 324 of the degraded image 320 is substantially identical to the same zone of the stored image 300.

In the embodiment described herein, "substantially identical" is objectively defined to mean that the average SSIM index that is calculated between the clear zone 324 of the degraded image 320 and the corresponding zone of the stored image 300 is at least equal to 0.9.

The degraded zone 323 may furthermore be considered to be using an optimal degradation parameter corresponding to peripheral vision if the average SSIM index calculated between the first blurred-zone 311 and the point-of-interest 301 (or between the point-of-interest zone 321 of the degraded zone 323 and the corresponding zone of the point-of-interest 301 in the stored image 300) is advantageously comprised between 0.4 and 0.8, preferably between 0.4 and 0.7, and for example between 0.45 and 0.65, in order to promote visual exploration. Such a degradation in particular guarantees that the peripheral region will contain enough information to incite a visual and tactile exploration, and not an excessive amount of information, so that the peripheral region is indeed representative of the corresponding decrease in visual acuity.

Too low an average SSIM index removes too much information from the degraded zone 323 to incite optimal exploration. Too high an average SSIM index does not remove enough information from the degraded zone 323 to ensure the subject makes, with his finger, an exploration that faithfully reproduces his ocular exploration.

The average SSIM index between the point-of-interest 301 and the degraded zone 311 will be referred to as the SSIMm index below. A typical procedure for calculating the SSIMm index for a set of points-of-interest 301 begins with selecting a set of regions-of-interest from the stored image 300. The set is made up of salient zones. For example, in the case of a photograph, salient zones are tied to regions on which the camera was focused. Blurry and/or uniform regions are generally of little interest to the subject performing a visual exploration. The blurred zones 311 of the integrally-degraded image 310 correspond to these regions of interest 301.

The calculation proceeds with converting the regions of interest 301 and the blurred zones 311 into a finite number of luminance levels. A convenient number of luminance levels is $2^8$.

The procedure continues with locally calculating an SSIM index is calculated with parameters K1=0.01 and K2=0.03 using a symmetric and circular Gaussian weighting window of 11×11 pixel size and 1.5 pixel standard deviation. This results in a map map Issim of SSIM indices that is interpolated to the dimensions of the regions of interest 301 and of the blurred zones 311. As a result, there is one SSIM-index value per pixel. These are used to calculate an average value SSIMm of the SSIM-index values in the regions of interest.

It is particularly advantageous if the clear zone's area is small enough so that the movements of the subject's finger are able to faithfully reproduce his eye movements. If S1 designates the area of the clear zone 324 and S2 the area of the degraded image 320, such as that displayed on the touch display 11, the ratio S1/S2 is preferably at most equal to 0.5, or even at most equal to 0.15. This promotes a need to move the finger, and hence the point-of-contact, to carry out visual exploration. Preferably, S1 is at most equal to sixty square centimeters, and preferably at most equal to twenty-five square centimeters. Beyond these dimensions, the clear zone 324 will possibly be considered to have too large an area with respect to foveal vision.

The ratio S1/S2 is preferably at least equal to 0.01, or even at least equal to 0.02. This enables the clear zone 324 to be sufficiently discernible by the subject so that visual adaptation is not excessively strenuous for the subject. When the subject is a child, or when a stylus is to be used, the ratio S1/S2 may be lower. Such a dimension of the clear zone 324 is also suitable for a touch display 11 of small size with a relatively low resolution. Preferably, S1 is at least equal to two square centimeters, and preferably at least equal to three square centimeters. The clear zone 324 preferably includes a circle of a diameter of at least eight millimeters above the point-of-contact 325, and preferably of at least twelve millimeters above that point.

Figure 13:
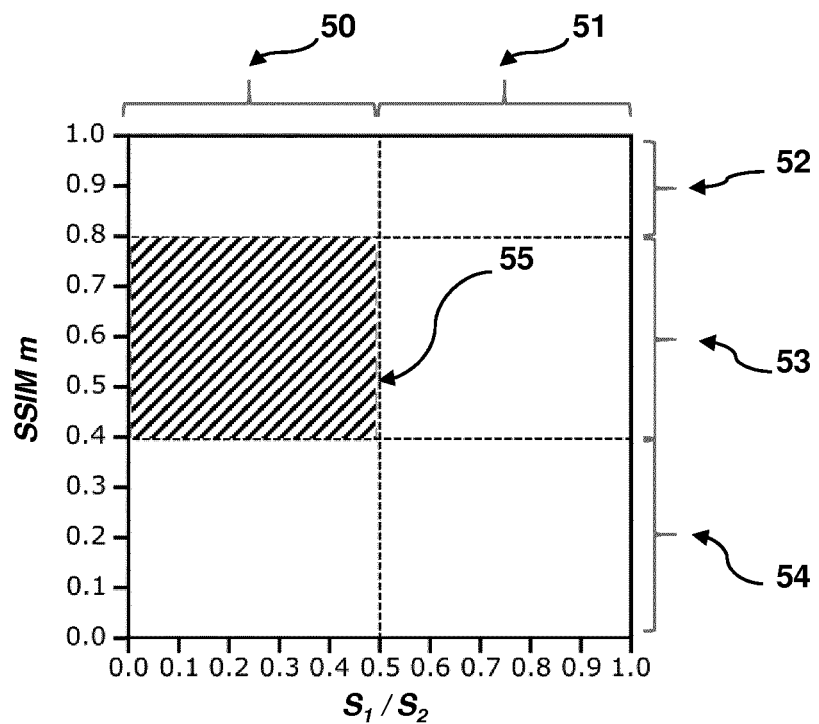
FIG. 13 is a graph illustrating parameters guaranteeing an optimal ocular exploration by way of the device.

FIG. 13 is a graph schematically illustrating parameters guaranteeing an optimal ocular exploration by way of the device. The graph shows the ratio S1/S2 on the horizontal axis, and the parameter SSIMm on the vertical axis (between the point-of-interest 301 and the first blurred-zone 311). The zone corresponding to the reference 55 allows an optimal visual exploration with a good fidelity between the movement of the finger and the eye movements. The zone 50 corresponds to the requirement that the area of the clear zone 324 not exceed a maximum, inducing a touch exploration that faithfully reproduces the visual exploration. The zone 51 corresponds to a clear zone 324 that is too large for the touch exploration to faithfully correspond to the visual exploration. The zone 52 corresponds to a degradation in the degraded zone 323 that is insufficient to lead to a touch exploration that is faithful to the visual exploration. The zone 53 corresponds to a degradation suitable for removing the microstructures of the point-of-interest 301, while preserving the main structures. Such a degradation turns out to be suitable for soliciting a touch exploration. The zone 54 corresponds to an excessive degradation of the image in the degraded zone 323, for example corresponding to a loss of macrostructures in the zone 321. Such an excessive degradation adversely affects both the visual exploration and the touch exploration.

A very wide variety of image degradation methods may be used. It is in particular possible to envision degrading the stored image 300 to generate the degraded zone 323 by applying a Gaussian blur, by applying an averaging filter, by applying sub-sampling, or by JPEG encoding with a very high degree of compression.

FIG. 12 schematically illustrates a partially-degraded image 400 in which the points-of-interest of the stored image are alphanumeric characters. The image 400 includes a clear zone 404 including a point-of-contact 405 of the subject with the touch display. Clear alphanumeric characters may be seen within the zone 404. Outside of the clear zone 404, there is a degraded zone 403 including degraded alphanumeric characters 406. The characters 406 are here decipherable but the degradation applied in practice is advantageously carried out so as to make them localizable but unreadable, in order to incite exploration. The dimensions of the clear zone 404 may be tailored to the dimensions of the alphanumeric characters, the clear zone possibly for example including between 1 and twenty alphanumeric characters in total. The size of the clear zone 404 may be parameterizable, for example in order to allow the subject to be prompted and to incite him to read a text.

Tests have been carried out to confirm the excellent correlation between the ocular exploration measured by oculometry, and the touch exploration measured by a method according to the invention. To do this, the touch exploration with a method for determining ocular movement according to the invention has been compared with an ocular exploration performed with a reference oculometry device.

The parameters of the reference ocular exploration experiment, in which ocular exploration was measured by oculometry, were as follows. This reference ocular exploration experiment was carried out with a system sold under the trade name TOBII Series 50, associated with the data-preprocessing software package sold under the trade name Clearview. Tests were carried out on 5 healthy subjects.

The protocol of presentation of a plurality of test images followed the following procedure includes displaying a fixation cross on the screen and, after some interval, pressing a button to trigger the experiment, displaying, beforehand, a fixation cross for one second on the screen, displaying and permitting free exploration of a non-blurry test image for six seconds, and returning to the initial displaying step.

A total of sixty-six images were presented to each subject on a screen of 1280×1024 pixel resolution, with an eye-screen distance of 60 cm (i.e. about 40 pixels/degree of visual angle). The resolution of each image was optimized for display, without modification, on screens of 1280×1024 and 1366×768 resolution.

The stimuli or points-of-interest were selected to include two series of images representing human social scenes (thirty-two images) or social scenes of monkeys of various species (thirty-four images).

Human social scenes were selected because a good understanding of a social scene requires a specific ocular exploration behavior that is predictable and easily quantifiable; because optimal ocular exploration of a social scene requires an intact cognitive capacity; because deficient ocular exploration of a social scene may be an indication of a potentially handicapping cognitive disorder; and because difficulties in understanding established social scenes are present in many psychiatric and neurological pathologies (pervasive developmental disorders, autism, schizophrenia, dementia, etc.).

The eye movements were modeled with a saccade/fixation model using the preprocessing software package. Only fixations of a duration of 100 milliseconds or more were retained in the analyses. For each subject and each image, a heat map was estimated by kernel density estimation (a.k.a the Parzen-Rosenblatt method) using a Gaussian kernel of 500-pixel variance ($\sigma \approx 22.4$ pixels$\approx 0.5°$ of visual angle) that was weighted by the fixation time. Lastly, a heat map was calculated for each stimulus as the average of the normalized individual heat maps.

The heat maps obtained were indeed characteristic of the ocular exploration of social scenes. Healthy subjects correctly detected the various protagonists of the social scenes. Usually, where appropriate, the subjects have a tendency to focus on the region of the eyes.

The determination of ocular movements by way of touch exploration was implemented as follows. Each image was displayed on a touchscreen of a resolution of 1366 by 768 pixels. For each stored image, a degraded image was generated, in order to simulate the decrease in spatial resolution between foveal vision, parafoveal vision, and peripheral vision. This simulation of decrease in spatial resolution was carried out while preserving a clear zone at the point-of-contact and in its surroundings in order to simulate foveal vision. The clear zone was dimensioned to correspond to a cone half-angle of 2° with respect to the eye of the subject, i.e. to a circle of a radius of 80 pixels. The clear, and therefore foveal, zone and the parafoveal zone were generated by applying a Gaussian window of a standard deviation of 2° or 80 pixels in this example. Peripheral vision was simulated by applying a Gaussian blur with a standard deviation of 1° outside of the parafoveal zone.

For ergonomic reasons, the clear zone was positioned, in the degraded image, in a position slightly above the determined point-of-contact with the touchscreen (25 pixels). Color information was integrally preserved in the degraded image.

The touch exploration was recorded with the x- and y-axis coordinates of each point-of-contact and the duration of continuous contact at this point-of-contact.

An ocular pseudo-fixation may be determined when the contact at a point-of-contact is maintained for a length of time longer than one sampling period Tr. Each pseudo-fixation may be recorded, with its position and its duration of contact.

If the points of contact change continually, the successive coordinates of the points of contact are recorded at intervals corresponding to the sampling period Tr.

The value of the sampling period Tr may be a compromise between, on the one hand, the temporal resolution required to achieve a good recording of the touch movement, and on the other hand, the touch capacities of the recording device. A sampling period Tr comprised between 20 and 30 milliseconds proved to be suitable; a sampling period comprised between 10 and 50 milliseconds may for example be envisioned. For a device having a low image refresh rate and/or a high processing capacity, much lower sampling-period values may be used.

The measurement of the points of contact of the subjects with the touchscreen indeed made it possible to characterize that the movement of the finger on the degraded image corresponded, with a very good correlation, to a visual exploration behavior.

The touch exploration according to the invention revealed finger movements that were slower than the eye movements measured by oculometry. The respective exploration times of each image were adapted to the two types of exploration, in order to make them comparable. The touch exploration may for example be interrupted after a preset time that is longer than a preset time used in the oculometry test. The touch exploration duration is advantageously at least equal to 2 seconds and for example at least 5 seconds.

It is also possible to envision defining the duration of the touch exploration by interrupting it only when a touch exploration distance threshold has been crossed. This distance threshold may for example be expressed in terms of a number of pixels or of a cone half-angle. The touch exploration distance may be set on the basis of an average visual-exploration distance covered by a group of subjects in a length of time of 6 seconds. In the tests carried out, this distance was for example estimated to be 2500 pixels per image, with an approximate standard deviation of 500 pixels.

For each subject and each image, a speed index was calculated for each pseudo-fixation (except the first). This calculation was carried out by dividing the distance covered between two successive pseudo-fixations (of index n−1 and n for example), by the duration of the last of these two pseudo-fixations (that of index n in this example).

For each image, it is possible to envision excluding very rapid pseudo-fixations from the analysis, with a view to optimizing computing time. Specifically, it may be estimated that very rapid pseudo-fixations correspond to pseudo-saccades that provide little information. For each image, it is for example possible to envision excluding from the analysis the fastest 20% of the pseudo-fixations.

Similarly to the oculometry test, for each subject and each image, a heat map was estimated by kernel density estimation (a.k.a the Parzen-Rosenblatt method) using a Gaussian kernel of 500 pixel variance ($\sigma \approx 22.4$ pixels$\approx 0.5°$ of visual angle) that was weighted by the pseudo-fixation time. Lastly, a heat map was calculated for each stimulus as the average of the normalized individual heat maps. A heat map was calculated for each stimulus as the average of each of the heat maps of each subject for this image.

The heat maps obtained by oculometry and by touch exploration were observed to be very similar. It was in particular observed that the heat maps of the two methods clearly reflected pseudo-fixations on the same points-of-interest of an image.

A first quantitative index was used to quantify the heat maps obtained using the two methods. This first index was a simple measurement of correlation between the heat maps obtained using the two methods. Correlation values comprised between 0.341 and 0.849 were observed for images of human social scenes. Correlation values comprised between 0.385 and 0.893 were observed for images of simian social scenes. Such correlation values are high enough to guarantee the fidelity of the touch exploration with respect to the ocular exploration. Generally, images illustrating a plurality of living beings will be favored for the tests, in order to include social scenes, in particular for applications to the identification of disorders.

The touch exploration according to the invention therefore faithfully reproduces ocular exploration, in particular because the touch exploration uses a biomimetic approach, simulating the processing carried out in the retina of the subject.

The variability in the correlation scores seems to be more related to the complexity of the tested image than to a real difference in exploration behavior between the two methods. Specifically, the more complex an image, the more the subject has a tendency to make random movements in his strategy of discovery of an image.

Having described the invention, and a preferred embodiment thereof, what we claim as new and secured by Letters Patent is:

1. An apparatus for determining eye movement, said apparatus comprising a touch display, a memory, and a processor configured to repeat a set of steps, wherein said set of steps comprises determining a position of a contact point at which a user touches said display, said position being a determined position, locating a corresponding portion in an image that is being displayed on said touch display, generating a degraded image based on a stored image, displaying said degraded image on said touch display, and recording successive positions of said contact point, wherein said degraded image is substantially identical to said stored image within a clear zone thereof, wherein said clear zone includes said determined position and surroundings thereof, wherein said stored image is degraded beyond said clear zone by a peripheral degradation parameter.

2. A method comprising determining eye movements, wherein determining eye movements comprises providing an apparatus, executing a set of steps and repeating execution of said set of steps, wherein said apparatus comprises a touch display and a memory that stores an image that includes a point of interest, wherein said image is a stored image, wherein said set of steps comprises determining a position of a contact point, locating a corresponding position in an image that is displayed on said touch display, generating a degraded image from said stored image, displaying said degraded image on said touch display, and recording successive positions of said contact point, wherein said contact point is a point at which a user contacts said touch display, wherein said degraded image is substantially identical to said stored image with a clear zone, wherein said clear zone includes said contact point and surroundings thereof, and wherein said image is degraded beyond said clear zone using a peripheral degradation parameter.

3. The method of claim 2, wherein generating said degraded image comprises blurring said stored image beyond said clear zone.

4. The method of claim 2, wherein generating said degraded image comprises causing an average SSIM index between the stored image and said degraded image to be between 0.4 and 0.8, wherein a ratio of an area of said clear zone to an area of said degraded image is between 0.01 and 0.5.

5. The method of claim 2, wherein generating said degraded image comprises causing an average SSIM index between the stored image and said degraded image to be between 0.4 and 0.7, wherein a ratio of an area of said clear zone to an area of said degraded image is between 0.01 and 0.15.

6. The method of claim 2, wherein said clear zone is a circle that has a diameter of at least eight millimeters around said contact point.

7. The method of claim 2, further comprising sampling said contact point following lapse of an interval since obtaining an immediately preceding sample of said contact point, wherein said interval is greater than or equal to ten milliseconds and less than or equal to fifty milliseconds.

8. The method of claim 2, further comprising, further comprising waiting for lapse of an interval after executing said set of steps and repeating said execution of said set of steps only after lapse of said interval, wherein said interval is at least five seconds long.

9. The method of claim 2, wherein said stored image illustrates a plurality of living beings, each of which forms a point of interest.

10. The method of claim 2, further comprising recording successive positions of said contact point and a reference visual exploration path, determining that a divergence between said successive positions of said contact point and said reference visual exploration path has exceeded a predetermined threshold, and, in response, drawing attention to an occurrence of a visual exploration anomaly.

* * * * *